United States Patent [19]

Butts

[11] 4,433,832

[45] Feb. 28, 1984

[54] METALLURGICAL LANCE

[75] Inventor: Douglas E. Butts, Brookpark, Ohio

[73] Assignee: Inland Enterprises, Inc., Cleveland, Ohio

[21] Appl. No.: 453,465

[22] Filed: Dec. 27, 1982

[51] Int. Cl.³ .............................................. C21D 11/00
[52] U.S. Cl. ....................................... 266/87; 266/88; 266/99; 266/225
[58] Field of Search ...................... 266/87, 225, 88, 99, 266/81, 86, 226; 75/60; 73/DIG. 9, 343

[56] References Cited

U.S. PATENT DOCUMENTS

| | | | |
|---|---|---|---|
| 3,264,874 | 9/1966 | Fischer | 266/88 |
| 3,413,852 | 12/1968 | Engel et al. | 266/225 |
| 3,565,412 | 2/1971 | Moniot | 266/225 |
| 3,598,386 | 8/1971 | Murphy | 266/87 |
| 4,367,868 | 1/1983 | Blom et al. | 266/225 |

FOREIGN PATENT DOCUMENTS 1273224 7/1968 Fed. Rep. of Germany ........ 266/88

Primary Examiner—L. Dewayne Rutledge
Assistant Examiner—S. Kastler
Attorney, Agent, or Firm—Thomas M. Schmitz

[57] ABSTRACT

A refractory clad metallurgical lance comprises a temperature sensing thermocouple means in combination with an internal gas conduit encased within exterior refractory cladding material wherein the conduit provides a passage way for transmitting inert gas under pressure. The thermocouple means is disposed within the refractory cladding and directed radially outward toward the outer peripherary of the refractory cladding whereby the temperature sensing portion is located near the peripheral surface of the cladding. The thermocouple is disposed within a ceramic protective tube which in turn is embedded within the refractory material secured around the internal gas conduit. In use, the metallurgical lance is operative to process molten metal by submerging the lower portion of the lance below the molten metal surface and bubbling inert gas through the metal while simultaneously directly measuring the temperature of the molten metal.

12 Claims, 3 Drawing Figures

METALLURGICAL LANCE

BACKGROUND OF THE INVENTION

This invention pertains to refractory clad metallurgical lances particularly useful in the processing of molten metal such as steel. Refractory clad metallurgical lances are shown in U.S. Pat. Nos. 3,292,622, 3,833,209, and 3,976,286.

Steel is produced in a refining vessel such as an electric or basic oxygen furnace. When the proper temperature and chemistries of the molten metal are achieved, the superheated steel is tapped from the furnace into a transfer ladle for the purpose of degassing the molten metal and performing related processing functions commonly known as temperature trimming to cool and stir the melt and to simultaneously insure a homogenous composition. In such stirring operations, a metallurgical lance is adapted to transmit inert gas such as nitrogen or argon under pressure to a nozzle portion of a metallurgical lance partially immersed in the molten metal. Argon gas is preferred to avoid nitrogen pickup by certain kinds of steel grades. In use, the lance is inserted within the ladle until the lowermost portion of the lance containing a discharge opening is disposed below the molten steel whereby agitation of the molten metal becomes vigorous due to pressurized gas passing through the lance and bubbling through the molten metal. The temperature of the molten metal is taken periodically during the stirring process, by an expandable thermocouple which is then discarded after each use. After various trimmings have been performed, additional temperatures must be taken. Temperature control is necessary to obtain the intended chemical and metallurgical results as well as consistently high quality steel. Depending on how and where the steel is treated following the ladle transfer, the molten metal must be maintained above certain critical temperature or minimum temperature to avoid metallurgical problems which can occur if the melt is too cold during the stirring process step. Expendable batch thermometers or thermocouples, however, are costly and provide only instantaneous temperature readings and often provide misleading temperature measurements due to cooling. Temperature control is unsatisfactory due to intermittent spot readings. The expendable thermometers are destroyed in use thus requiring several thermometers to be used in the manufacture of a single batch of steel. U.S. Pat. No. 3,413,852 suggests an oxygen lance containing a plurality of radiometers adapted to indirectly measure molten metal surface temperatures and radiation gas passing through the oxygen lance. Such radiometers, however, are expensive devices and merely provide indirect measurement of molten metal temperatures causing inaccuracies associated with radiation measurements such as emissivity corrections, convection losses, heat transfer errors, molten metal surface phenomena and related discrepancies inherent with indirect radiation measurements of molten steel by optical measuring methods.

Accordingly, it is highly desirable to provide a means for directly measuring temperature of molten metal accurately and for continuously monitoring the direct melt temperature during the stirring process, and to further provide such means for direct and continuous temperature measurements in combination with the matallurgical lance. The refractory cladding effectively withstands the extremely high heat, turbulence of the molten metal, thermal stresses due to rapid heating and cooling as well as chemical erosion, which can cause premature failure of the metallurgical lance. Even more advantageous, it now has been found that a thermocouple imbedded within the refractory material of a refractory clad metallurgical lance can provide accurate and continuous direct temperature measurements of the molten metal simultaneously with the operation of the lance, and additionally overcomes the problem of using numerous expendable thermocouples.

SUMMARY OF THE INVENTION

Briefly, this invention pertains to a metallurgical lance comprising a linear metal tube or metal conduit encased within a refractory cladding material and further containing a thermocouple means secured within the refractory material, whereby the refractory material protects both the thermocouple and the lance while the nozzle portion of the lance is submerged under molten metal. In accordance with this invention, a thermocouple means is imbedded within the refractory clad material incasing the linear metal tube adapted to bubble argon, nitrogen, or other inert gas through the molten metal. The thermocouple sensing device is orientated laterally outward from the linear metal tube so that the temperature sensing portion of the thermocouple is disposed closest to the outer periphery of the refractory cladding. The refractory cladding maintains an integral exterior surface whereby the thermocouple junction temperature sensing means is fully protected by the refractory cladding and yet accurately and directly measures the molten metal temperature while emersed in the molten metal.

The thermocouple imbedded within the refractory of the refractory clad metallurgical lance advantageously provides a continuous temperature indication at a remote operator's location during the processing of steel or iron while argon gas is injected into the metallurgical melt to control the melt temperature, desulfurization, and the ladle general metallurgical process. The refractory clad lance containing an imbedded thermocouple in accordance with this invention advantageously provides continuous service of the thermocouple during the life of the lance itself and will survive as long as the refractory remains intact and protects the metal lance, which can be as high as forty heats of argon stirring. The imbedded thermocouple senses a direct heat temperature of the molten metal and can be adapted to provide a remote reading by proportioned electrical output lead wires. These and other advantages of this invention will become more apparent from the drawings and the detailed description of the invention.

IN THE DRAWINGS

DETAILED DESCRIPTION OF THE INVENTION

Figure 1:
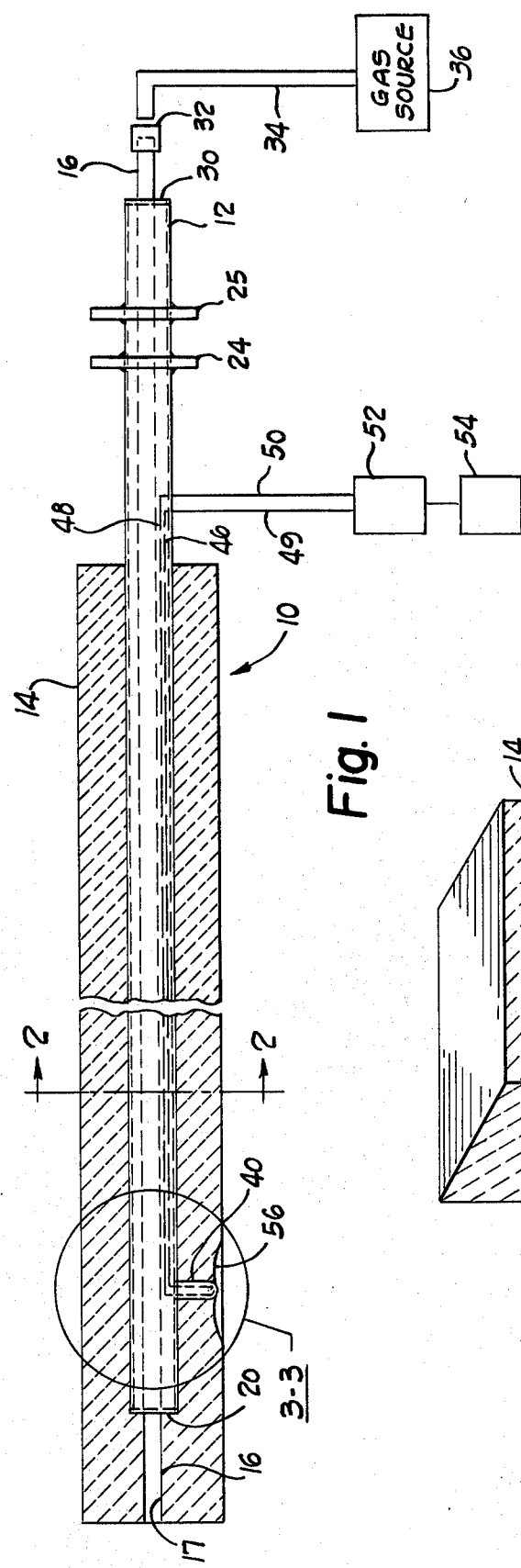
FIG. 1 is a vertical partial cross-section of the refractory clad metallurgical lance containing an imbedded thermocouple in accordance with this invention.
Figure 2:
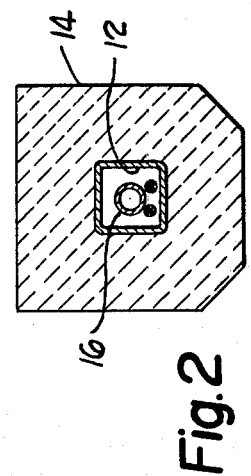
FIG. 2 is a section view taken along line 2—2 in FIG. 1.

Referring now to the Drawings wherein like characters designate like parts, shown is a refractory clad metallurgical lance 10 comprising a linear conduit preferably containing an interior pipe 16 disposed within outer tubular steel 12 encased within refractory cladding material 14. The tubular steel 12 is shown as a square cross-section but can be circular or other cross-sectional shape. The outer tubular steel 12 contains the interior pipe 16 shown as circular but can be other suitable cross-section shapes. At the upper protion of the lance 10, the outer tube 12 and interior pipe 16 together extend beyond the refractory cladding material 14 whereas the bottom portion of the lance 10 is totally encased with the refractory material except for the provision of a discharge opening 17 or nozzle portion of the lance 10. The outer tube 12 terminates a distance from the nozzle portion 17 but the interior pipe 16 continues downwardly, becomes encased within the refractory cladding 14, and terminates at the distal bottom portion forming the nozzle discharge opening 17 of the lance 10.

As shown in FIG. 1, the interior pipe 16 is secured in a spaced relationship with the surrounding outer tube 12 by a steel plate washer 20 welded to the bottom end of the outer tubing 12 whereby the interior pipe 16 is maintained centrally spaced within outer tube 12 and in a radically spaced relationship relative to the square outer tube 12. The air space between interior pipe 16 and outer tube 12 advantageously provides an air space between the refractory and the interior pipe 16 to further insulate the interior pipe 16 from the extreme heat of molten metal. The refractory cladding 14 extends upwardly encasing the square outer metal tubing 12 but teminates at a point about two-thirds up the linear outer tubing 12. Thus, the refractory material 14 is secured to and covers the conduit means comprising the outer tube 12 and the interior pipe 16 over the depth that the lance 10 can be immersed within the molten steel melt while the lance 10 is in use. The outer tube 12 extends upwardly from the refractory cladding 14 where two vertically spaced oversized steel plates 24, 25 are welded to the exterior square tubing 12. At the uppermost terminis of the outer square steel tubing 12 a welded steel washer 30 maintains the interior circular pipe 16 centrally secured within the outer square tubing 12. The upper end of the interior circular pipe 16 has a coupling 32 adapted to interconnect with feed piping 34 and a source 36 of argon or nitrogen gas under pressure whereby the inert gas can be fed under pressure through the hollow interior circular pipe 16 from top to bottom and provides the desired bubbling action while the lowermost refractory portion of the lance is immersed in molten steel in use.

Typically, the outer square steel tubing 12 can be 3" by 3" and $\frac{1}{4}$" thick. The interior circular pipe 16 can be $\frac{3}{8}$" schedule 40 pipe. The square tubing can be about 16' to 17' in length and can be typically spaced about 6" to 12" upwardly from the bottommost end of the refractory 14 but extends upwardly and beyond the top of the refractory at the upper portion of the lance 10. The interior steel pipe 16 extends beyond both ends of the outer square tubing 12 and typically can be about 17' to 18' in overall length. The refractory material can be high alumina refractory containing reinforcing steel fiber or similar structural fibers and advantageously should provide about $2\frac{1}{2}$" to 3" thick refractory cladding around the cladded lower portion of the lance 10. The refractory desirably should extend about 13 to 14 feet although longer or shorter cladding can be used depending on the desired design. Wires or other anchoring means can help secure the refractory cladding 14 to the outer space tubing 12 such as shown in U.S. Pat. No. 3,976,286.

Figure 3:
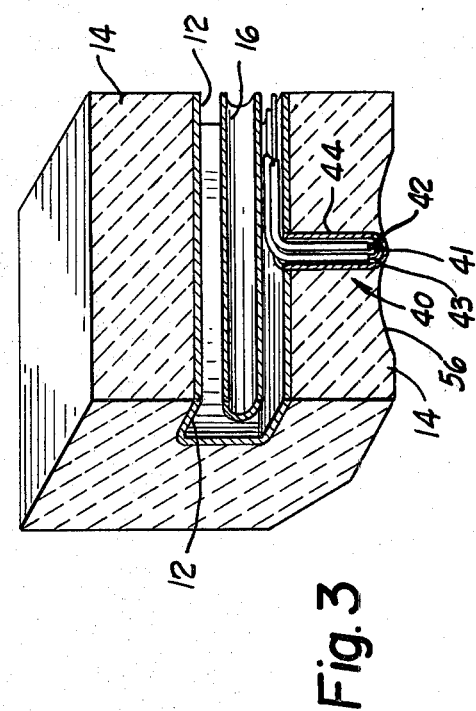
FIG. 3 is an enlarged view of a portion of the lance shown in FIG. 1 indicated 3—3 and particularly showing the thermocouple imbedded within the refractory material.

In accordance with this invention, a thermocouple means 40 comprises platinum rodium thermocouple juncture 41 imbedded within the cast refractory wall 14 in the lower portion of the lance 10 as indicated generally in FIG. 1 and best viewed in FIG. 3. The thermocouple juncture 41 can be a Type B thermocouple preferably or a Type R, or Type S, or similar type thermocouple. A Type B thermocouple for instance comprises a welded juncture 41 between two different platinum alloy wires such as 6% rodium-platinum alloy wire 42 and 30% rodium-platinum alloy wire 43. The thermocouple means 40 extends laterally into the refractory wall 14 and terminates at a point about 90% through the wall thickness or about $\frac{1}{4}$" but at least $\frac{1}{8}$" from the outer periphery of the refractory wall 14. Preferably, the thermocouple means 40 is contained within a separate ceramic sheathe or refractory tube member 44 such as shown in U.S. Pat. No. 4,093,193 or similar preformed refractory tubes for high temperature thermocouple devices. The preformed refractory tube 44 can be laterally directed or radially disposed within the cast refractory cladding 14 while assembling the uncured casting material prior to hardening the castable refractory material in conjunction with the square tubing 12. In this manner, the outer terminis of the preformed refractory tube 44 for the thermocouple can be located close to the outer peripheral surface of the refractory cladding 14, as best shown in FIG. 3, without weakening the refractory cladding 14. The platinum alloy wires 42, 43 of thermocouple means 40 secured within the preformed refractory tube 44 interconnects with a pair of copper or copper alloy insulated lead wires 46, 47 which in turn extend upwards within the refractory cladded portion of the lance 10. The lead wires 46, 47 preferably are located in the air space between the outer tube 12 and the inner pipe 16, although the wires 46, 47 can be located adjacent to the outside wall of the tubing 12 and/or imbedded within the refractory 14 adjacent to the outer wall of the tubing 12. The copper alloy lead wires 46, 47 extend upward within the lance 10 and eventually extend away from the lance 10 by copper alloy insulated extension wires 49, 50. The extension wires 49, 50 interconnect to a direct temperature readout 52 or a continuous temperature recorder 54 or similar recording means displaying the temperature on a continuous basis.

The lance 10 can be assembled in a conventional manner by casting refractory material around the outer square tubing 12 containing the inner circular pipe 16 secured in a spaced relationship within the outer tubing 12. The thermocouple means 40 can be secured within refractory sheath 44 which in turn is secured within the castable material as described above, whereby the copper lead wires 46, 47 are preferably disposed within the air space between interior pipe 16 and outer tube 12. By locating the insulated lead wires 46, 47 within the air space the wires 46, 47 are maintained cool and avoids undersirable heating which can cause a secondary thermocouple effect and create erroneous temperature readings.

In use, the lance 10 is immersed in the molten metal contained within a ladle or other vessel for containing molten steel to the extent that only a portion of the refractory clad lance 10 is disposed below the molten metal surface while the uncladded exposed steel tubing 12 portion is maintained well above the molten metal surface. Inert gas such as argon is piped under pressure from a source to the inner pipe 16 of lance 10 through the coupling 32 secured at the uppermost portion of the inner circular pipe 16. Gas is transmitted through the hollow inner pipe 16 and exists through the lowermost distal end nozzle portion 17 of the inner pipe 16 whereby the gas bubbles through the molten steel causing a stirring and cooling effect on the molten metal. The thermocouple means 40 is likewise disposed below the molten metal surface whereby the direct temperature of the molten metal can be sensed without errors introduced by indirect temperature measurements of the melt. The direct temperature of the molten metal is transmitted by lead wires 46, 47 disposed within the air space between interior pipe 16 and the outer tube 12 and connected with extension wires 49, 50 interconnected with a remotely located external temperature display means where temperatures are continuously recorded.

In a preferred embodiment of this invention, the refractory cladding contains an indented or concave area 56 surrounding the distal tip of the thermocouple refractory tube or sheathe 44 as shown in FIG. 1 and best viewed in FIG. 3. The concave area 56 typically can be between a ¼ and ½ inch radius whereby the distal tip of the refractory tube 44 is preferably flush with the concave surface 56 and directly exposed to molten metal in use. Although not as desirable, the refractory thermocouple tube 44 can protrude slightly beyond the concave surface 56, but not beyond the outer peripheral surface of the refractory cladding 14, or alternatively the refractory thermocouple tube 44 can be slightly recessed from the concave surface 56. The recessed concave surface 56 permits molten metal to flow adjacently to the thermocouple juncture 41 located within the ceramic or refractory tube 44 without exposing the refractory tube 44 to breakage due to the tube 44 protruding outwardly from the refractory cladding 14 outer peripheral surface. The concave surface 56 advantageously provides protection for the refractory tube 44 within the refractory cladding 14 and yet maintains proximate exposure of the thermocouple juncture 41 to the molten metal. Hence, temperature, measurement errors due to the influence of surrounding refractory cladding 14 or the temperature of the refractory cladding 14 itself are advantageously avoided and the direct meaasurement of the molten metal is directly sensed by the thermocouple means 40 in the refractory tube 44 directly exposed to molten metal.

Accordingly, the refractory clad lance of this invention containing an internal thermocouple means secured within the refractory cladding advantageously provides accurate direct temperature measurement of the molten metal on a continuous basis without the need for expendable thermocouples. The lance and thermocouple combination is adequately protected by the refractory cladding material whereby the lance and self-contained thermocouple of this invention can be used continuously during a single stirring operation, and can be used over and over again without failure for several separate stirring operations. The scope of this invention is not restricted except by the appended claims.

I claim:

1. A refractory clad metallurgical lance for injecting gas into molten metal by emersing the lower nozzle portion of the lance into the molten metal, the lance comprising:
    a linear metal conduit having an outer refractory cladding material encasing at least the lower portion of the metal conduit wherein the refractory cladding contains a nozzle discharge opening communicating with said metal conduit to form a nozzle portion, whereby the metal conduit is adapted to transmit inert gas to the nozzle portion of the lance;
    thermocouple means disposed within said refractory cladding in the lower portion of the lance, said thermocouple means disposed within a refractory protective tube directed radially outwardly from said metal conduit and within said refractory cladding material, said protective tube having an outermost tip portion within said refractory cladding material adjacent to the exterior peripheral surface of the refractory cladding material, said tip portion containing a thermocouple joint for continuously measuring the temperature of the molten metal while the lance is disposed in the molten metal; and
    said metal conduit comprising an interior metal pipe disposed within an exterior tube and secured thereto in a radially spaced relationship to provide an air space between the interior pipe and the outer tube, said outer tube encased within said refractory cladding material, said thermocouple means having lead wires disposed in said air space between the interior pipe and the outer tube and connected to an exterior temperature indicator.

2. A refractory clad metallurgical lance for injecting gas into molten metal by emersing the lower nozzle portion of the lance into molten metal, the lance comprising:
    a linear metal conduit having outer refractory cladding material encasing at least the lower portion of the metal conduit wherein the refractory cladding contains a nozzle discharge opening communicating with said metal conduit to form a nozzle portion, whereby the metal conduit is adapted to transmit inert gas to the nozzle portion of the lance;
    thermocouple means disposed within said refractory cladding in the lower portion of the lance, said thermocouple means directed outwardly toward the exterior peripheral surface of the exterior refractory cladding for continuously measuring the temperature of the molten metal while the lance is disposed in the molten metal, and said thermocouple means adapted to record the temperature measured by the thermocouple means;
    said metal conduit comprising an interior metal pipe disposed within an outer tube and secured thereto in a radially spaced relationship to provide an air space between the interior pipe and the outer tube, said outer tube encased within said refractory cladding material, and said thermocouple means including lead wires in said air space and connected to an exterior temperature indicator;
    said thermocouple means disposed within a refractory protective tube secured within the exterior refractory cladding material,
    wherein the protective tube containing thhe thermocouple means has an outermost tip portion, and said refractory cladding material contains an indented surface to expose said tip portion of the protective tube.

3. The lance in claim 2 wherein the indented surface is concave.

4. The lance in claim 2 wherein the exposed tip portion protrudes slightly from the concave surface.

5. The lance in claim 2 wherein the protective tube is disposed radially outward from the tube and secured within the exterior refractory cladding material.

6. The lance in claim 2 wherein the thermocouple means contains a thermocouple joint located within the protective tube at the outermost extended portion of the protective tube toward the outer peripheral surface of the refractory cladding material.

7. A refractory clad metallurgical lance for injecting gas into molten metal by emersing the lower nozzle portion of the lance into the molten metal, the lance comprising:

a linear metal conduit having outer refractory cladding material encasing at least the lower portion of the metal conduit wherein the refractory cladding contains a nozzle discharge opening communicating with said metal conduit to form a nozzle portion, whereby the metal conduit is adapted to transmit inert gas to the nozzle portion of the lance;

thermocouple means disposed within said refractory cladding material in the lower portion of the lance, said thermocouple means directed outwardly toward the exterior peripheral surface of the refractory cladding for continuously measuring the temperature of the molten metal while the lance is disposed in the molten metal, said thermocouple means adapted to record the temperature measured by the thermocouple means; and said thermocouple means disposed within a refractory protective tube having an outermost tip portion, and said encasing refractory cladding material contains an indented surface adjacent to the outermost tip portion of the said protective tube.

8. The lance in claim 7 wherein the indented surface in the refractory cladding comprises a concave surface surrounding the outermost tip portion of the protective tube.

9. The lance in claim 7 wherein the distal tip portion of the protective tube is substantially flush with said concave surface.

10. The lance in claim 7 wherein the distal tip portion of the protective tube protrudes slightly beyond the concave surface but not beyond the outer peripheral surface of said refractory cladding material.

11. The metallurgical lance in claim 7 wherein the protective tube is secured radially outwardly from said metal conduit and within the refractory cladding material.

12. The lance in claim 7 wherein the thermocouple means contains a thermocouple joint located within the protective tube at the outermost tip portion.

* * * * *